US00PP36396P2

(12) United States Plant Patent
Vermeulen-van der Vegt

(10) Patent No.: US PP36,396 P2
(45) Date of Patent: Jan. 14, 2025

(54) ***AGAPANTHUS* PLANT NAMED 'HPP4087'**

(50) Latin Name: *Agapanthus praecox*
Varietal Denomination: HPP4087

(71) Applicant: Highlands Potplants V.O.F., 's-Gravenzande (NL)

(72) Inventor: Jolien Vermeulen-van der Vegt, Rozenburg (NL)

(73) Assignee: HIGHLANDS POTPLANTS V.O.F., 'S-Gravenzande (NL)

( * ) Notice: Subject to any disclaimer, the term of this patent is extended or adjusted under 35 U.S.C. 154(b) by 0 days.

(21) Appl. No.: 18/679,391

(22) Filed: May 30, 2024

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
CPC ..... A01H 6/04; A01H 5/02
See application file for complete search history.

*Primary Examiner* — Keith O. Robinson
(74) *Attorney, Agent, or Firm* — Penny J. Aguirre

(57) ABSTRACT

A new cultivar of *Agapanthus* plant named 'HPP4087' that is characterized by its floriferous and re-blooming habit, its early flowering season, its compact plant habit, and its efficient propagation.

2 Drawing Sheets

Botanical classification: *Agapanthus praecox*.
Varietal denomination: 'HPP4087'.

BACKGROUND OF THE INVENTION

The present invention relates to a new and distinct cultivar of *Agapanthus praecox* and will be referred to hereafter by its cultivar name, 'HPP4087'. 'HPP4087' represents a new perennial grown for landscape and container use.

The new cultivar was derived from a controlled breeding program by the Inventor in 's-Gravenzande, Netherlands. The goal of the breeding program was to develop a new cultivar of *Agapanthus* that re-blooms, reliably blooms and is floriferous with a compact plant habit. The Inventor made a cross in June of 2013 between unnamed and unpatented proprietary plants of *Agapanthus* from the Inventors breeding program; reference no. 12-0027 as the female parent and reference no. 10-0104-004 as the male parent. The Inventor selected 'HPP4087' in June of 2015 as a single unique plant amongst the seedlings that resulted from the above cross.

Asexual propagation of the new cultivar was first accomplished by tissue culture utilizing meristematic tissue under the direction of the Inventor in 's-Gravenzande, The Netherlands in June of 2022. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'HPP4087' as a distinct cultivar of *Agapanthus*.

1. 'HPP4087' exhibits a floriferous and re-blooming habit.
2. 'HPP4087' exhibits an earlier flowering season.
3. 'HPP4087' exhibits a compact plant habit.
4. 'HPP4087' exhibits efficient propagation.

The female parent of 'HPP4087' differs from 'HPP4087' in having a shorter plant height, less inflorescences, and in lacking a re-bloom habit. The male parent of 'HPP4087' differs from 'HPP4087' in having a less compact plant habit, more narrow leaves, less inflorescences, and in lacking a re-bloom habit. 'HPP4087' can be most closely compared to the *Agapanthus* cultivars 'Little White' (not patented) and 'Snow Pixie' (not patented). 'Little White' is similar to 'HPP4087' in being floriferous and in blooming early in the season. 'Little White' differs from 'HPP4087' in having a less compact plant habit, leaves that are more narrow and longer in size, weak peduncles, and in lacking a re-blooming habit. 'Snow Pixie' is similar to 'HPP4087' in being floriferous with numerous inflorescences. 'Snow Pixie' differs from 'HPP4087' in having a less compact plant habit, shorter peduncles, smaller inflorescences with less flowers per inflorescence, and in lacking a re-blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102 (b) (1) for disclosures and/or sales that fall within a one-year grace period to the filing date. Disclosures include website listings by Global Flowers, Floral Daily, The Big Plant Nursery, vida-verde, Noviflora, R.H.S., Hamiplant, Bunkers Hill Plant Nursery, Substack, Matelma, Shoot Gardening, Blomsterlandet, Plantarium Groen-Direkt, floragard, avaxaplants, karaolawogrodzie, PlatformGroen, Dio Flowers, Tuinadvies, TuinVAK, Florca, GuiaVerde, AIPH, duboiplantes shop, Horisberger Yvorne SA, Greenport Boskoop, FloraXchange, KVBC, Boom in Business, Tuincentrum Tullekensmolen Beekbergen, and IL Floricultore.

BRIEF DESCRIPTION OF THE DRAWINGS

The accompanying color photographs illustrate the overall appearance and distinct characteristics of the new *Agapanthus*. The photographs were taken of 16-month-old plants of 'HPP4087' as grown outdoors in a 17-cm container in 's-Gravenzande, Netherlands.

The photograph in FIG. 1 provides a side view of a plant of 'HPP4087' in bloom.

Figure 1:
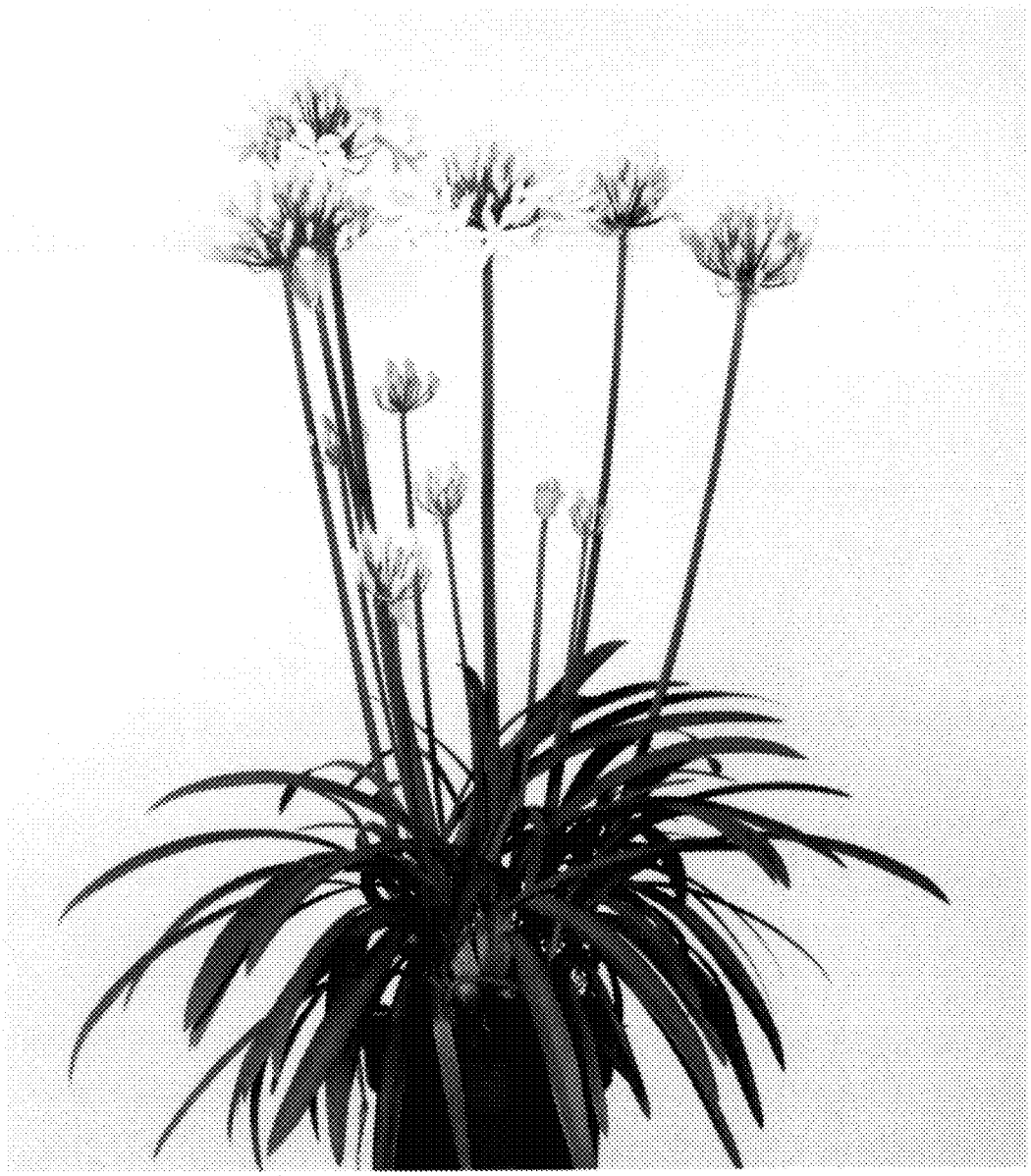
Figure 2:
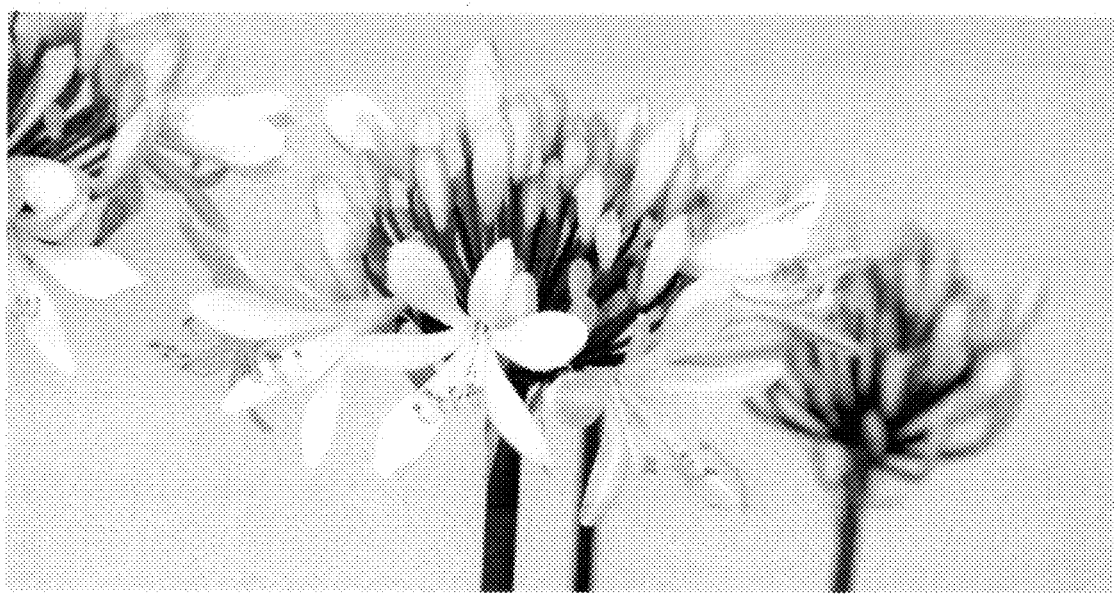

The photograph in FIG. 2 provides a close-up view of an inflorescence of 'HPP4087'.

Figure 3:
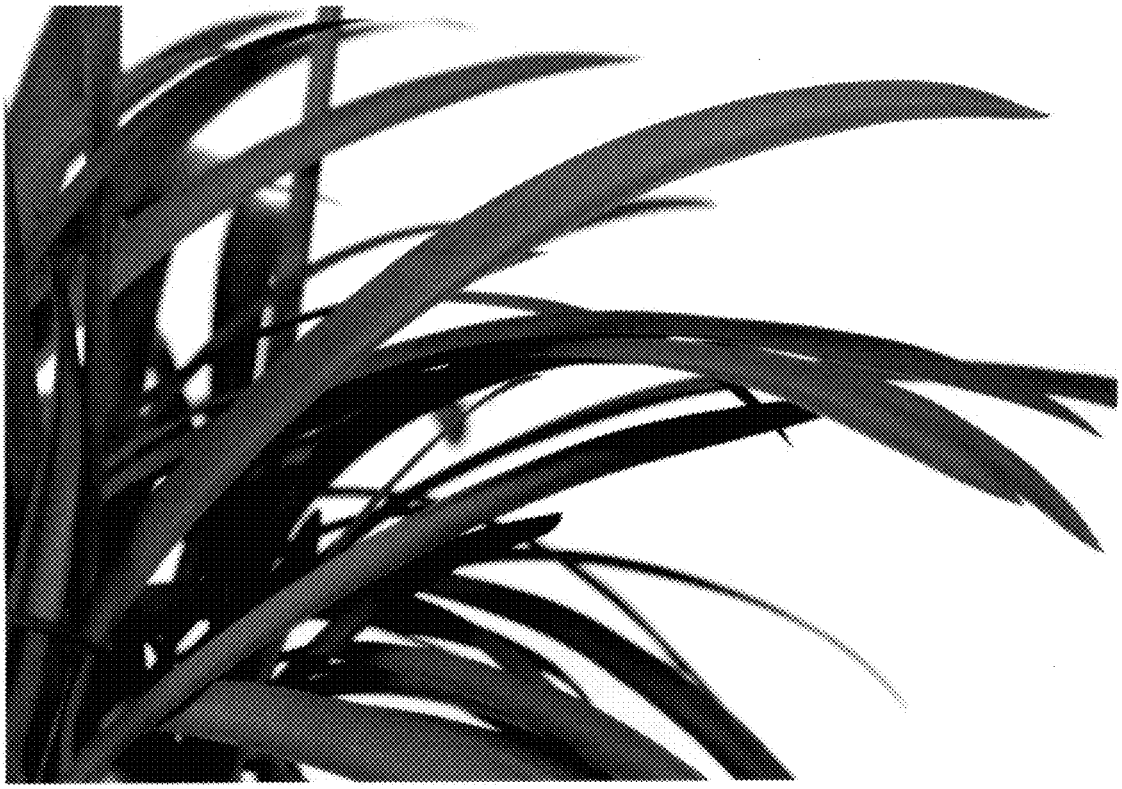

The photograph in FIG. 3 provides a close-up view of the foliage of 'HPP4087'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 16-month-old plants of 'HPP4087' as grown outdoors in 17-cm containers in 's-Gravenzande, Netherlands. The phenotype of the new cultivar may vary with variations in environmental, climatic, and cultural conditions, as it has not been tested under all possible environmental conditions. The color determinations are in accordance with the 2019 Colour Chart of The Royal Horticultural Society, London, England, except where general color terms of ordinary dictionary significance are used.

General description:

*Blooming period*.—Early summer into midsummer in The Netherlands.

*Plant type*.—Herbaceous perennial, semi-evergreen in colder climates.

*Plant habit*.—Compact, basal rosettes with inflorescences emerging from the rosette center.

*Height and spread*.—Soil level to top of foliar plane; 26.6 cm, soil level to top of floral plane; 62.5 cm, spread; 56.2 cm as a 16-month-old plant grown in a container.

*Hardiness*.—At least in U.S.D.A. Zones 8 to 12.

*Diseases and pests*.—No susceptibility or resistance to diseases or pests has been observed.

*Root description*.—Thick and fleshy.

*Propagation*.—Tissue culture.

*Root development*.—About 10 weeks for root initiation and 10 weeks for a cutting to fully root as a young plant.

*Growth rate*.—Moderate.

*Number of shoots (rosettes)*.—An average of 14.

Foliage description:

*Leaf shape*.—Ligulate.

*Leaf division*.—Simple.

*Leaf base*.—Decurrent, broadly cuneate.

*Leaf arrangement*.—In basal rosettes, equitant.

*Leaf apex*.—Acute.

*Leaf aspect*.—Emerging leaves erect, then cascade.

*Leaf venation*.—Parallel, upper surface; NN137A and NN137B, lower surface; 144B.

*Leaf margins*.—Entire.

*Leaf size*.—Up to 31.8 cm in length and up to 1.8 cm in width.

*Leaf surface*.—Smooth, glabrous, upper surface is matte to very slightly glossy, lower surface is matte.

*Leaf number*.—Average of 6 leaves per rosette.

*Leaf color*.—Young leaves upper surface; 143A, young leaves lower surface; 143C, margins 138A, mature leaves upper surface; 137A to 137B, mature leaves lower surface; 143B, margins 137B.

*Leaf attachment*.—Sessile to base.

*Leaf density*.—Dense.

Flower description:

*Inflorescence type*.—Umbel.

*Flower fragrance*.—None.

*Flower type*.—Rotate, campanulate.

*Flower number*.—An average of 75 flowers per umbel.

*Inflorescence size*.—Average of 8.1 cm in height and 13.3 cm in diameter.

*Flower size*.—An average of 3.9 cm in depth, 4.4 cm in diameter, throat; 3.9 cm in length, 4.5 mm in diameter, tube; 1.2 cm in length, 5 mm in diameter.

*Lastingness of inflorescence*.—Average of 2 weeks, self-cleaning.

*Flower aspect*.—Upward, outward to downward.

*Peduncle*.—Strong, oval in shape, held primarily upright, average of 50.1 cm in length, 7 mm in diameter, surface is glabrous and glaucous surface covered with a very thin, matte, waxy layer 138B in color, with glaucous layer scraped off; a blend of 143A and 146A.

*Pedicels*.—Strong, oval in shape, held in various angles to peduncle, average of 2.7 cm in length, 1.25 mm in diameter, surface is glabrous, smooth, and moderately glossy, color; 143A, at the base of each individual pedicel, a single bract is present; filiform in shape, 2.3 cm in length, 2 mm in width, both surfaces 164D in color.

*Flower buds*.—Oblanceolate in shape, average of 2.3 cm in length and 6 mm in diameter, color; 155C, top 157B, base 145D.

*Flower bract*.—Immature inflorescences covered with a single bract; broadly ovate in shape, acuminate apex, truncate base, 4.1 cm in length, 2.2 cm in width, upper surface color 27A, lower surface color 165C to 165D.

*Tepals*.—6, oblanceolate in shape, entire margins, acute apex, both surfaces glabrous and slightly velvety, moderately thick substance, an average of 4 cm in length and 9 mm in width, color: when opening upper surface; NN155D, main vein NN155B, when opening lower surface; NN155D, central stripe and main vein NN155B, lower tepal slightly tinged NN155A at the top, when fully open upper surface; NN155D, veins NN155B, when fully open lower surface NN155D, lower tepal NN155B, veins NN155B, tube color: outer surface 155C, inner surface 155C, base 145D, throat color: NN155D, veins NN155.

*Calyx*.—Rotate, 3.4 cm in length, 4.4 cm in diameter.

Reproductive organs:

*Gynoecium*.—Pistil; 1, average of 2.7 cm in length, stigma; club-shaped, 1 mm in length, 0.5 mm in diameter, 154D in color, style; 2.6 cm in length, NN155D in color, ovary; 145A to 145B in color.

*Androecium*.—Stamens; 6, anthers; dorsifixed and oblong in shape, average of 2.25 mm in length, 0.75 mm in width, 9A in color, filament; 2.9 cm in length, NN155D in color, pollen; moderate in quantity, 13A in color.

*Staminodes and pistillodes*.—Not present.

*Fruit/seed*.—Have not been observed to date.

It is claimed:

1. A new and distinct cultivar of *Agapanthus* plant named 'HPP4087' as herein illustrated and described.

* * * * *